(12) United States Patent
Xie et al.

(10) Patent No.: US 11,920,176 B2
(45) Date of Patent: Mar. 5, 2024

(54) **METHOD FOR PRODUCING BIOGAS FROM WASTE LIQUID/RESIDUE AFTER DIOSGENIN EXTRACTION FROM *DIOSCOREA COMPOSITA* BY ALUMINUM CHLORIDE**

(71) Applicant: SOUTH CHINA AGRICULTURAL UNIVERSITY, Guangdong (CN)

(72) Inventors: Jun Xie, Guangdong (CN); Guican Bi, Guangdong (CN); Hongdan Zhang, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 0 days.

(21) Appl. No.: 18/026,593

(22) PCT Filed: Nov. 27, 2020

(86) PCT No.: PCT/CN2020/132079
§ 371 (c)(1),
(2) Date: Mar. 16, 2023

(87) PCT Pub. No.: WO2021/068992
PCT Pub. Date: Apr. 15, 2021

(65) Prior Publication Data
US 2023/0257784 A1  Aug. 17, 2023

(30) Foreign Application Priority Data

Oct. 10, 2019  (CN) .......................... 201910957377.9

(51) Int. Cl.
*C12P 5/02* (2006.01)
*C07J 71/00* (2006.01)

(52) U.S. Cl.
CPC .......... *C12P 5/023* (2013.01); *C07J 71/0005* (2013.01)

(58) Field of Classification Search
None
See application file for complete search history.

(56) References Cited

FOREIGN PATENT DOCUMENTS

| CN | 1792894 | | 6/2006 |
|---|---|---|---|
| CN | 1792894 | A * | 6/2006 |
| CN | 102464431 | | 5/2012 |
| CN | 104478706 | | 4/2015 |
| CN | 105084638 | | 11/2015 |
| CN | 110643640 | | 1/2020 |

OTHER PUBLICATIONS

Singh, R. P., Surendra Kumar, and C. S. P. Ojha. "A critique on operational strategies for start-up of UASB reactors: effects of sludge loading rate and seed/biomass concentration." Biochemical engineering journal 1.2 (1998): 107-119. (Year: 1998).*
Bao, J., and L. Wang. "Removal of High-Concentration and Refractory Organic Matter from Diosgenin Manufacture Wastewater: a case study of a demonstration project in Hubei Province, PR China." AGU Fall Meeting Abstracts. vol. 2009. 2009. (Year: 2009).*
Luo Bin et al., "Research of Characters on Biogas Production of the Yam Residue Anaerobic Digestion in Different Bacteria", Environmental Science & Technology, with English abstract, Apr. 2015, pp. 33-39.
Miao Li- Hong et al., "Research and Application on the Utilization of Diosgenin Solid Waste and Wastewater by Composting", Hubei Agricultural Sciences, with English abstract, Mar. 2007, pp. 218-221.
Wang Yan-Jie et al., "Experimental studies for levulinic acid production from diosgenin solid waste", Journal of Northwest A & F University, with English abstract, Sep. 2010, pp. 141-147.
Ye Chen et al., "Inhibition of anaerobic digestion process: A review", Bioresource Technology 99, Jul. 2008, pp. 4044-4064.
Guangying Ye et al., "Ethanol production from mixtures of sugarcane bagasse and Dioscorea composita extracted residue with high solid loading", Bioresource Technology, Feb. 2018, pp. 23-29.
S. Xie et al., "Effect of pig manure to grass silage ratio on methane production in batch anaerobic co-digestion of concentrated pig manure and grass silage", Bioresource Technology, Mar. 2011, pp. 5728-5733.
"International Search Report (Form PCT/ISA/210) of PCT/CN2020/132079," dated Mar. 3, 2021, with English translation thereof, pp. 1-5.
"Written Opinion of the International Searching Authority (Form PCT/ISA/237) of PCT/CN2020/132079," dated Mar. 3, 2021, with English translation thereof, pp. 1-10.

* cited by examiner

Primary Examiner — Robert J Yamasaki
(74) Attorney, Agent, or Firm — JCIPRNET (57) ABSTRACT

Disclosed is a method for producing biogas from a waste liquid/residue after diosgenin extraction by aluminum chloride. Specifically, in a fermentation vessel, an anaerobic sludge and a waste residue from diosgenin extraction by aluminum chloride are added at a volatile solids ratio of (1-3):(1-2), or a seeding sludge and a diosgenin waste liquid are added with an organic loading having a VS:COD ratio of (1-2):(1-2); and then the above components are fermented at 35-37° C. for 5-25 d such that biogas is produced. According to the method of the present invention, the maximum cumulative biogas production rates are 255.4 mL/g VS for waste residue and 326.9 mL/g COD for waste liquid, and throughout the fermentation period, ammoniacal nitrogen values are below 1500 mg/L and pH variation is within the normal range, and the COD removal rate for the fermentation broth is 91.11%.

9 Claims, 4 Drawing Sheets

METHOD FOR PRODUCING BIOGAS FROM WASTE LIQUID/RESIDUE AFTER DIOSGENIN EXTRACTION FROM *DIOSCOREA COMPOSITA* BY ALUMINUM CHLORIDE

CROSS-REFERENCE TO RELATED APPLICATION

This application is a 371 application of International PCT application serial no. PCT/CN2020/132079 filed on Nov. 27, 2020, which claims the priority benefit of China application no. 201910957377.9, filed on Oct. 10, 2019. The entirety of each of the above mentioned patent applications is hereby incorporated by reference herein and made a part of this specification.

TECHNICAL FIELD

The present invention relates to the technical field of resource utilization of wastes extracted from plants, and in particular to a method for producing biogas from a waste liquid/residue after diosgenin extraction from *Dioscorea composita* by aluminum chloride.

DESCRIPTION OF RELATED ART

Steroid hormone drugs have achieved significant effects in anti-tumor, regulating immune system and treating diseases of cardiovascular system, rheumatic diseases, bacterial encephalitis and diseases of skin. Therefore, various countries in the world have rapidly developed studies on steroid hormones. However, the industrialization development road of steroid hormones is facing the problems of scarce source of drugs, low content in raw materials and expensive artificial synthesis, which is thus incapable of satisfying the demands for large-scale and mass production. The discovery of diosgenin has initiated a precedent of synthesizing steroid drugs with *Dioscorea* plants as raw materials, thus promoting the research progress of the development and utilization of *Dioscorea* plant resources. The carbon skeleton structure of diosgenin is exactly similar to that of a steroid hormone drug, and it is the most ideal precursor to synthesize steroid hormone drugs. Diosgenin, industrially called saponin, is linked to carbohydrates in sites C-3 and C-26 thereof via glycosidic bonds and exists in plants in the form of a steroid saponin. Therefore, diosgenin has good market prospect and development values for the research and production on the extraction and preparation from *Dioscorea* resources.

The existing preparation technologies for diosgenin mainly include two methods based on chemical hydrolysis and bio-hydrolysis, and some assisted extraction and preparation technologies or multiple methods-combined technologies are derived therefrom. The biotransformation of saponins into diosgenin via the combination of a biological method and enzymolysis has been concerned by numerous researchers due to free environmental pollution, but compared with the conventional direct acid hydrolysis, the application of the process is limited in the diosgenin industry due to diseconomy of enzyme preparations and low efficiency of biotransformation. Currently, most of domestic diosgenin manufacturers still perform mass production with the conventional way of direct acid hydrolysis. Moreover, because the conventional acid hydrolysis is usually performed with concentrated sulfuric acid, the waste liquid produced after isolation has stronger acidity and thus is difficult to be treated.

Organic waste liquid and solid waste residue in the diosgenin industry are usually discharged and discarded directly without treatment, which not only pollutes the environment and occupies cultivated land, but also causes waste of resources. The residual waste in the production of diosgenin contains lots of starch, cellulose and other organic substances. Miao Lihong, et al. have performed the following research: yellow ginger diosgenin waste residue and high-concentration diosgenin waste liquid are used as major raw materials to produce an organic fertilizer in a way of high-temperature composting fermentation; through pot and field experiments, it is verified that the organic fertilizer fermented by waste residue has highly qualified quality, thus providing a very effective method for the resource utilization of waste residue. Wang Yanjie, et al. have carried out the following study under normal pressure and acid catalysis; starch and cellulose in the *Dioscorea zingiberensis* waste residue are used as raw materials to prepare a green platform compound, levulinic acid, and the maximum yield is up to 18.31%. Ye, et al. have performed a study on the fermentation of cellulosic ethanol with *Dioscorea composita* waste residue and bagasse as raw materials; under the conditions of 34% material load and simultaneous saccharification and fermentation, the maximum concentration and yield of ethanol are up to 82.83 g/L and 77.22%, respectively. The production of diosgenin waste liquid is mainly focused on the acidolysis filtration and neutralization washing, and the waste liquid acidity (pH) generally ranges from 0.7 to 2.5. The waste liquid contains water-soluble saponins, pigment and monosaccharides from starch hydrolysis such that the diosgenin waste liquid has deep color and contains a large number of organic matters, and COD is up to 20000-110000 mg/L. The chemical method mainly includes three technical routes, namely, chemical neutralization, chemical oxidation flocculation, and adsorption. The COD removal rate can be generally up to 50% above, and there is certain room for improvement. Moreover, there is no report on producing biogas from waste liquid/residue after diosgenin extraction from *Dioscorea composita* at present.

SUMMARY

The objective of the present invention is to overcome the above shortcomings and disadvantages in the prior art; provided is a method for producing biogas from a waste liquid/residue after diosgenin extraction from *Dioscorea composita* by aluminum chloride.

The above objective of the present invention is achieved by the following technical solutions:

a method for producing biogas from a waste liquid/residue after diosgenin extraction by aluminum chloride; in a fermentation vessel, an anaerobic sludge and a waste residue from diosgenin extraction by aluminum chloride are added at a volatile solids ratio of (1-3):(1-2), or a seeding sludge and a diosgenin waste liquid are added with an organic loading having a VS:COD ratio of (1-2):(1-2); and the above components are subjected to fermentation at 35-37° C. for 5-25 days to produce biogas.

Preferably, the fermentation is performed with stirring for 1-2 min (preferably 1 min) at intervals of 5-6 min (preferably, 5 min).

Preferably, the fermentation temperature is 37° C.

Preferably, the fermentation lasts for 5-15 days (preferably 10 days).

Preferably, the seeding sludge has a pH value of 7.3-7.8 and a COD of 1000-1200 mg/L.

Preferably, the volatile solids ratio of the anaerobic sludge to the waste residue from diosgenin extraction by aluminum chloride is 3:1; the VS:COD ratio of the seeding sludge to the diosgenin waste liquid is 1:1.

Preferably, the diosgenin extraction by aluminum chloride includes as follows: putting a dried *Dioscorea* powder to a reaction still, and adding a ternary biphase solution consisting of an aluminum chloride aqueous solution, ethanol and petroleum ether, and mixing well, performing reaction for 0.5-3.0 h at 130-180° C., and filtering a reaction liquid to remove residues, isolating a petroleum ether layer, then performing rotary evaporation, and performing recrystallization to obtain diosgenin. The preparation of *Dioscorea composita* diosgenin by acidolysis with a non-conventional acid, namely, a lewis acid $AlCl_3$, in a ternary biphase system not only improves the yield of diosgenin and shortens the extraction cycle, but also greatly reduces the consumption of acid. Moreover, in case of no concentrated sulfuric acid, the process of the present invention minimizes the environmental pollution. The maximum yield of diosgenin has been up to 3.21%, and the growing rate of the yield of diosgenin obtained is 22.05% higher than that of the conventional sulfuric acid method, 67.19% higher than that of the ethanol-free biphase $AlCl_3$ hydrolysis, and even more than 2.7 times that of the biphase sulfuric acid hydrolysis.

Preferably, the reaction is performed at 140-170° C. for 1-2.5 h.

Preferably, the aluminum chloride aqueous solution has a concentration of 1.25 g/L-15 g/L.

Preferably, the ethanol/aluminum chloride aqueous solution/petroleum ether solution has a volume ratio of (6-15):16:(8-32).

Preferably, an additive amount of the *Dioscorea* powder in the reaction system is 18-20 g/L.

Preferably, the *Dioscorea* is *Dioscorea composita*.

Compared with the prior art, the present invention has the following beneficial effects.

The present invention provides a method for producing biogas from a waste liquid/residue after diosgenin extraction from *Dioscorea composita* by aluminum chloride. Different from the ways of the prior art, such as production of levulinic acid or ethanol by using *Dioscorea composita* waste residue, the present invention employs aluminum chloride to replace concentrated sulfuric acid for hydrolysis. The waste liquid produced after isolation has no $SO_4^{2-}$ ions and has relatively weak acidity. Compared with the waste liquid extracted from a conventional concentrated acid, the waste liquid of the present invention is treated more easily, thereby improving the reliability of the biogas production via anaerobic fermentation of the diosgenin waste liquid. According to the method of the present invention, the maximum cumulative biogas production rates are 255.4 mL/g VS for waste residue and 326.9 mL/g COD for waste liquid, and throughout the fermentation period, ammoniacal nitrogen values are below 1500 mg/L and pH variation is within the normal range, and the COD removal rate for the fermentation broth is 91.11%. The method of the present invention combines diosgenin production and anaerobic fermentation technologies to achieve comprehensive utilization of *Dioscorea composita* resources, which is capable of helping achieve green and sustainable development of the diosgenin industry.

DESCRIPTION OF THE EMBODIMENTS

The present invention will be further described with reference to the accompanying drawings and detailed examples of the description, but the examples are not construed as limiting the present invention in any form. Reagents, methods and equipment used herein are conventional regents, methods and equipment in the art, unless otherwise specified.

Reagents and materials used in the examples below are purchased from the market, unless otherwise specified.

Experimental materials: triennial *Dioscorea composita* tuber, derived from a *Dioscorea composita* planting base in Wengyuan County of Guangdong province. The triennial *Dioscorea composita* tuber was cut into slices, and then lyophilized by a lyophilizer for 24 h to remove excessive moisture, and then ground into powder with a grinding miller, and placed into a sealing bag and the sealing bag was put to a thermostatic water-removal sealer for storage and further use.

Diosgenin standard (≥99.9%, HPLC level) was purchased from US Fluka; chromatographically pure methanol was purchased from Sigma—Aldrich; analytically pure petroleum ether (60-90° C.) was purchased from Tianjin FUYU Fine Chemical Co., Ltd.; absolute ethyl alcohol, glucose, and aluminum chloride, analytically pure, were purchased from Shanghai Sinopharm Chemical Reagent Co., Ltd.; analytically pure sodium hydroxide was purchased from Guangzhou Chemical Reagent Factory; potassium sodium tartrate, sodium sulfite, Phenol, and 3,5-dinitrosalicylic acid, analytically pure, were purchased from Aladdin (Shanghai) Co., Ltd.

Seeding sludge: derived from Guangzhou Institute of Energy Conversion, Chinese Academy of Sciences and Guangzhou Datansha Sewage Treatment Plant; after being domesticated, the seeding sludge was subjected to starvation treatment one week before the anaerobic fermentation experiment.

Determination Indicator and Method (1) Analysis method of diosgenin: diosgenin extract after being metered and dissolved by methanol was diluted to certain folds, and then filtered with a 0.22 μm filter membrane, then the remaining solution was collected into a 1 mL sample bottle, and prepared into a sample for further use. Diosgenin standard (purity≥99.9%) from Fluka served as a control and subjected to high performance liquid chromatography (HPLC). Specific process was as follows: after being dissolved by methanol, the diosgenin standards at concentrations of $4.0\times10^{-3}$ mg/mL, $2.0\times10^{-2}$ mg/mL, $1.0\times10^{-1}$ mg/mL and 0.5 mg/mL were determined by high performance liquid chromatography; based on the chromatographic peak areas of the diosgenin standards, a standard curve was drawn; with the peak area as the sample quantitative basis, the diosgenin yield was calculated by the following formula: diosgenin $$\text{yield} = \frac{C \times 100\,\text{mL} \times N}{1000 \times W} \times 100\%,$$

where W: weight (g) of the raw material *Dioscorea composita*; C: concentration of diosgenin (mg/mL); N: dilution ratio. HPLC determination parameters: UV detector; C18 chromatographic column (4.6 mm×250 mm, 5 μm); column oven temperature: 40° C.; mobile phase: methanol/water; flow rate: 1.0 mL/min; loading volume: 10 μL. Each determination was repeated three times.

(2) VS: volatile solids refer to that total solids of a raw material subtracts ash content and other residues remaining in the muffle furnace after combustion. Measurement method: a sample with a weight (W) was placed into a muffle furnace for combustion for 2 h at 550° C., and cooled to 100° C. below, then put to a constant temperature and humidity drying vessel to be cooled to room temperature, and the weight was denoted as Wd. The formula for calculating VS in the sample is as follows:

$$VS = \frac{W - Wd}{W} \times 100\%.$$

(3) $NH_3$—N: organic nitrogen mainly exists in the form of free ammonia and ammonium ions after degradation during anaerobic fermentation; free ammonia may cross cytomembrane very easily to affect the balance between potassium ions and hydrogen ions inside and outside the cytomembrane, thus bringing the effect of ammonia-nitrogen toxicity inhibition. The generation of ammonia-nitrogen inhibition is affected by multiple conditions, but it is generally acknowledged that there is an obvious ammonia-nitrogen inhibition when the ammonia-nitrogen concentration is higher than 1700 mg/L in the anaerobic fermentation system (Chen et al., 2008; Xie et al., 2011). Determination of $NH_3$—N value: the extracted sample was centrifuged for 5 min at 8000 rpm and diluted, then 100 μL diluted solution was taken and an HACH ammonia-nitrogen reagent was added, where ultrapure water served as a blank control, then the solution was shaken up for reaction for 20 min, and then the ammonia-nitrogen value was determined with a DR2700 tester via zero setting of a null tube; and then the ammonia-nitrogen value of the sample was obtained by multiplying the ammonia-nitrogen value by the dilution ratio.

(4) COD: chemical oxygen demand is an important indicator to reflect the content of pollutants in water and is in positive correlation to the content of pollutants. Determination of the COD value: the extracted sample was centrifuged and diluted, then 200 μL of the diluted solution was added with an HACH COD prefabricated tube reagent (20-1500 ppm), and burned in an HACH COD digestion device for 120 min at 150° C., and then cooled; the COD value was determined with a DR2700 tester via zero setting of a null tube; and then the COD value of the sample was obtained by multiplying the COD value by the dilution ratio×10.

Example 1

(1) Preparation of diosgenin by hydrolysis of a ternary biphase $AlCl_3$: 5.0 g of the dried *Dioscorea composita* powder was added to a closed reactor; 80 mL 5.0 g/L aluminum chloride aqueous solution, 75 mL ethanol and 100 mL petroleum ether were added and mixed well, and subjected to reaction for 2.0 h at 160° C.; the reaction liquid was filtered to remove residues, and a petroleum ether layer was isolated, then rotary evaporation was carried out, and then recrystallization was performed to obtain *Dioscorea composita* diosgenin. The yield of the *Dioscorea composita* diosgenin was measured to be up to 3.21%; solid residue after the diosgenin extraction from *Dioscorea composita* by aluminum chloride was washed with water and dried, then stored in a drying vessel for further use; meanwhile, the low-acidic solution after the diosgenin extraction from *Dioscorea composita* by aluminum chloride was subjected to rotary evaporation to recover ethanol, and stored in a conical flask; the conical flask was sealed for further use. Properties of the *Dioscorea composita* waste liquid/residue and the seeding sludge are shown in Table 1:

TABLE 1

Properties of the *Dioscorea composita* waste liquid/residue and the seeding sludge

| Parameters | *Dioscorea composita* waste residue | *Dioscorea composita* waste liquid | Seeding sludge |
|---|---|---|---|
| VS (%) | 0.29 | — | 1.08 |
| pH | — | 2.55 | 7.3-7.8 |
| COD (mg/L) | — | 70000-80000 | 1000-1200 |

(2) Production of biogas from waste residue: an AMPTS® II full-automatic methane potential analysis system was used; the seeding sludge having an effective volume of 300 mL and the waste residue in the step (1) were respectively fermented in a fermentation flask having a total volume of 500 mL with an organic loading having VS ratios of 3:1, 2:1, 1:1 and 1:2, respectively via a 37° C. thermostat water bath. Stirring conditions were set as follows: stirring was performed for 1 min on time at intervals of 5 min, meanwhile, blank sludge served as a control; sampling was performed at the same period of time every day to monitor the fermentation; the measurement indicators include gas production rate, pH, $NH_3$—N, COD, and the like.

(3) Production of biogas from waste liquid: an AMPTS® II full-automatic methane potential analysis system was used; the seeding sludge having an effective volume of 300 mL and the diosgenin waste liquid were respectively fermented in a fermentation flask having a total volume of 500 mL with an organic loading having VS:COD ratios of 2:1, 1:1 and 1:2, respectively via a 37° C. thermostat water bath. Stirring conditions were set as follows: stirring was performed for 1 min on time at intervals of 5 min, meanwhile, blank sludge served as a control; sampling was performed at the same period of time every day to monitor the fermentation; the measurement indicators include gas production rate, pH, $NH_3$—N, COD, and the like.

Property Comparison

I. Comparison of Biogas Production from Waste Residue

1. Variation of the Accumulative Biogas Yield from Waste Residue at Different VS Ratios As can be seen from FIG. 1, the accumulative biogas yield of *Dioscorea* waste residue with different organic loadings under anaerobic fermentation increases with the fermentation time, and may be up to the peak value basically one week after the fermentation. For the fermentation experimental group with a higher organic loading, the occurrence of the peak value of the biogas yield delays accordingly.

Figure 1:
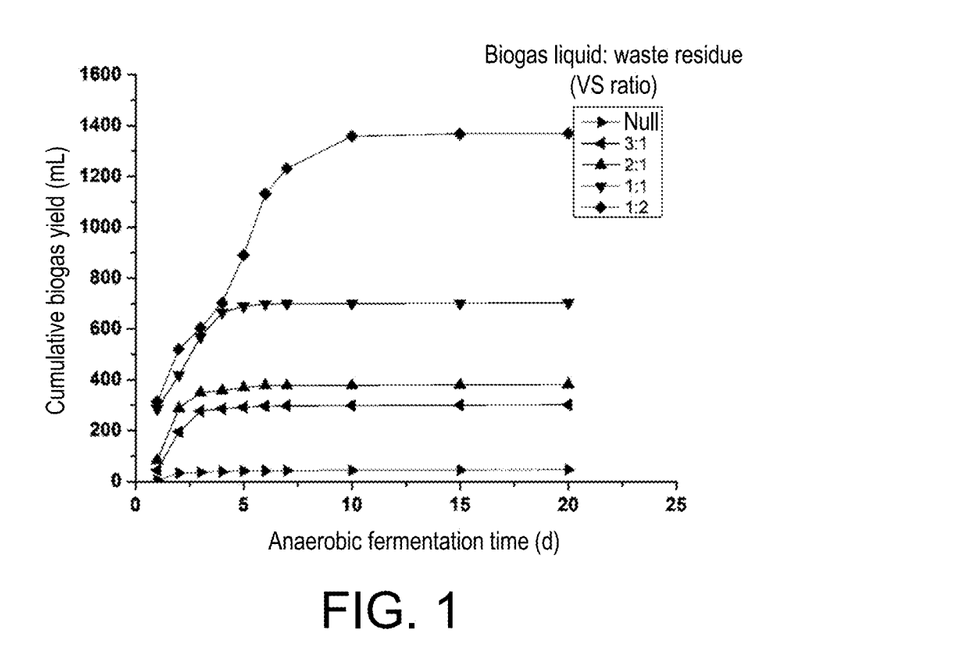
FIG. 1 shows a cumulative biogas yield from waste residue fermentation at different VS ratios.

When the fermentation is performed to the 10th day, all the fermentation experimental groups have been completed effective fermentation; the accumulative biogas yield and biogas production rate have no longer changed, and the cumulative curve is up to a stable and balanced linear state. At the end of the fermentation, organic loadings of all the experimental groups were averaged to obtain the cumulative biogas production rate of each experimental group. The results are as follows: 255.4 mL/g VS (3:1)>223.4 mL/g VS (2:1)>221.4 mL/g VS (1:1)>220 mL/g VS (1:2), respectively. Thus, as can be seen, when the organic loading is higher, the raw materials may not be fully degraded and transformed via fermentation such that the fermentation efficiency becomes low, which is thus incapable of achieving biogas yield and biogas production rate simultaneously. The reason why the high-load anaerobic fermentation system has low production efficiency may be as follows: a large number of organisms in the system were degraded to exceed the threshold value of the maximum transformation and utilization capacity of microbial flora in the anaerobic fermentation system, resulting the destroy of the acid-base balance. On the whole, $Dioscorea$ waste residue with different organic loadings has a better biogas production effect via anaerobic fermentation; when the load ratio is 3:1, the maximum biogas production rate may be achieved, being 255.4 mL/g VS.

Figure 2:
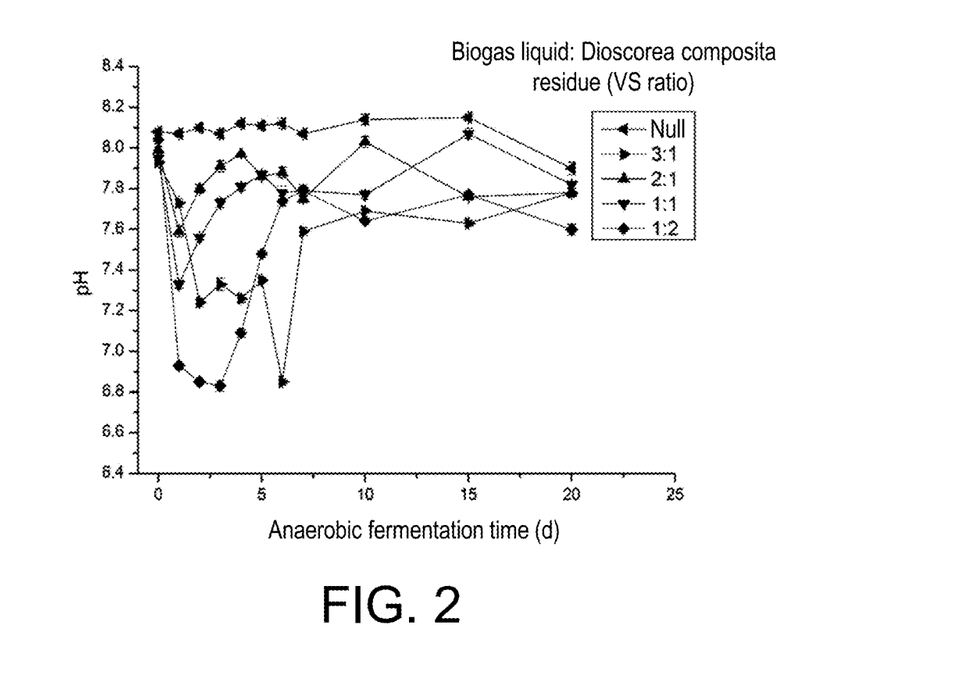
FIG. 2 shows pH variation during waste residue fermentation at different VS ratios.

2. Study on the Physical and Chemical Properties of Waste Residue with Different VS Ratios under anaerobic fermentation (1) pH Variation Throughout the anaerobic fermentation, pH is always an important indicator to indicate the stable operation of a system; pH directly reflects the running status of the system; too high or too low pH is against the production of biogas. FIG. 2 shows a pH variation curve in a waste residue fermentation flask; for the experimental groups with different VS ratios, the pH generally shows a trend of decreasing first and then increasing, which is basically consistent with the acid-base variation of the anaerobic fermentation in four stages. In the first stage of fermentation, because starch and other organic nutrients in $Dioscorea$ residue are hydrolyzed, acidized and degraded into small molecules, the pH value rapidly decreases starting from the first day of fermentation. Afterwards, under the combined action of acidolysis bacteria and obligatory anaerobic acetogenic bacteria, the pH value decreases continuously; moreover, for the experimental groups with different organic loading ratios, the pH value has different falling range; the higher the organic loading of the experimental group is, the larger the amplitude of dramatic pH variation is. In the final stage, under the utilization of methanogenic bacteria, acidic substances decrease gradually. Therefore, the pH value gradually increases and slowly tends to the pH of the blank group therewith, being about 7.8 on the 3rd day to the 7th day of the fermentation. To sum up, the pH variation of the $Dioscorea\ composita$ waste residue during anaerobic fermentation is kept within the normal range; there is no irreversible acidification caused by too low pH value, and the system is always in a steady operation status.

(2) $NH_3$—N Variation

Figure 3:
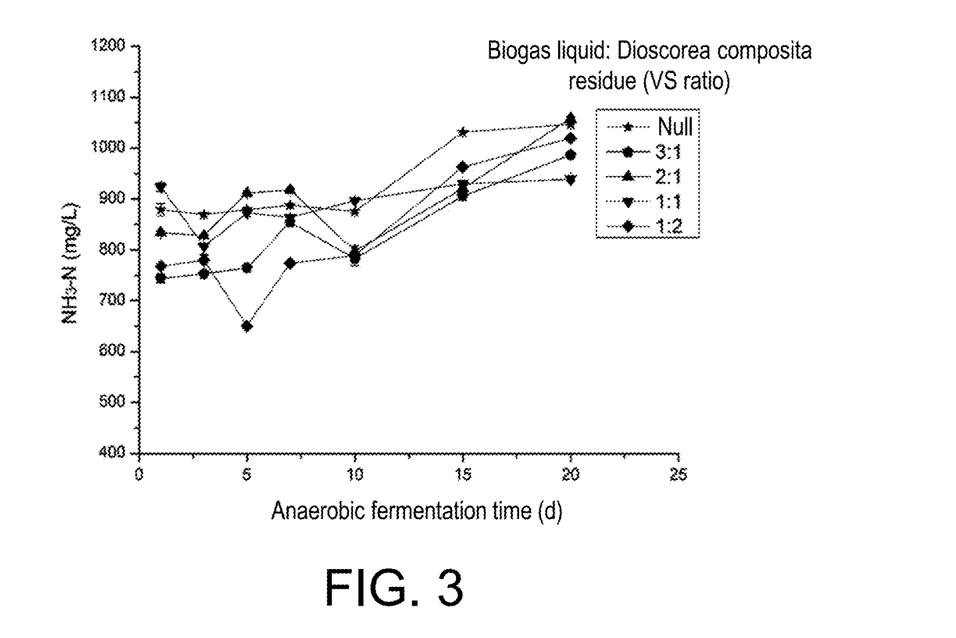
FIG. 3 shows $NH_3$—N variation during waste residue fermentation at different VS ratios.

The occurrence of $NH_3$—N inhibition is usually generated by a large number of free ammonias produced due to a lower carbon nitrogen ratio of the anaerobic fermentation system. Therefore, it is of great importance to choose the raw material with a suitable carbon nitrogen ratio for fermentation. When the concentration of $NH_3$—N is greater than 1500 mg/L, the system is believed ammonia poisoning, thus causing fermentation inhibition. As can be seen from FIG. 3, the $NH_3$—N variation trend of the waste residue fermentation at different VS ratios basically fluctuates around the blank group; the amplitude of variation is small and tends to be consistent with that of the blank group. Throughout the fermentation, ammonia-nitrogen values of all the experimental groups are lower than 1100 mg/L; the anaerobic fermentation system is in a steady status under self-regulation, and there is no fermentation inhibition. Meanwhile, the $NH_3$—N concentration is also closely related to the pH value of the system; the lower the pH value is, the lower the $NH_3$—N concentration is. Therefore, in the initial stage of the fermentation, the $NH_3$—N concentration is lower than that of the blank group, which is conducive to acid and biogas production. As the fermentation continues, the $NH_3$—N concentration increases slowly and tends to be stable gradually.

(3) COD Variation

Figure 4:
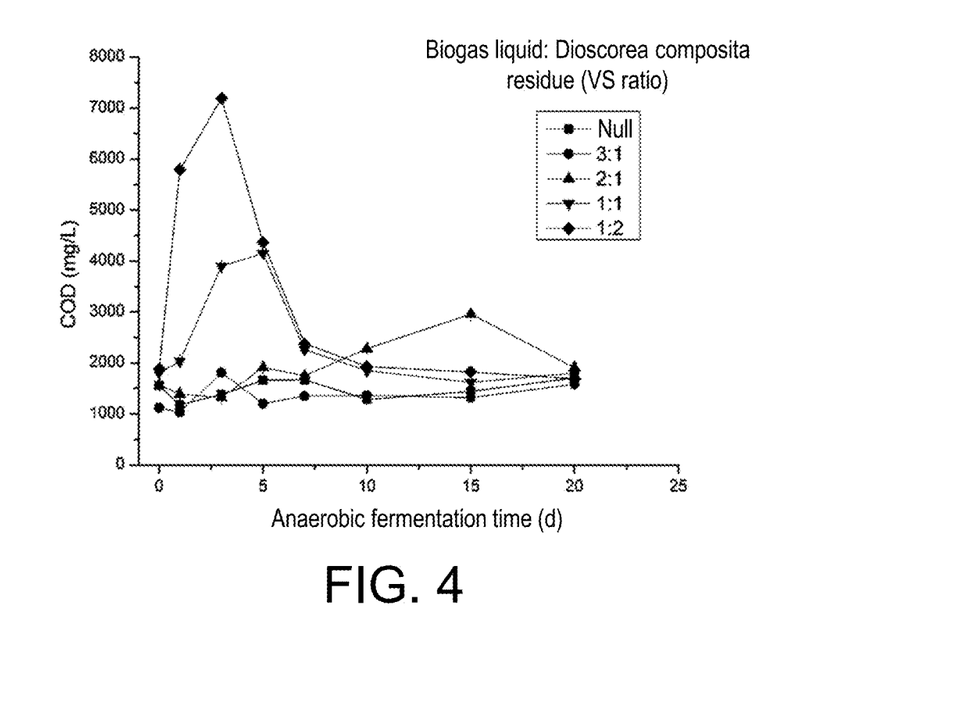
FIG. 4 shows COD variation during waste residue fermentation at different VS ratios.

The trend of the variation curve on the COD value under waste residue fermentation at different VS ratios is shown in FIG. 4. As can be seen, in a fermentation cycle, the COD values in all the experimental groups are basically the same at the beginning of the fermentation; this is because the solid waste residue is hardly dissolved into the fermentation broth at the beginning, and afterwards under the action of acidolysis bacteria and obligatory anaerobic acetogenic bacteria, starch and other macromolecular nutrients are gradually degraded into carbohydrates, acids and other substances, and accordingly the COD value increases gradually; later on, under the utilization of methanogenic bacteria, small molecule acids and other substances are gradually transformed into $CH_4$ and other gases to be discharged; therefore, the COD value decreases gradually again till recovers to the level of the blank sludge group. Further, as can be seen from FIG. 4, the higher the organic loading of the waste residue is, the greater the amplitude of increase of the COD value in the initial stage is, which indicates that there are more degraded carbohydrates, acids and other substances. At the end of the anaerobic fermentation, the COD value is 1500 mg/L around and recovers to the level of the blank sludge group after variation.

As can be seen from the above results: 255.4 mL/g VS (3:1)>223.4 mL/g VS (2:1)>221.4 mL/g VS (1:1)>220 mL/g VS (1:2); the pH variation of the $Dioscorea\ composita$ waste residue during anaerobic fermentation is kept within the normal range; there is no irreversible acidification caused by too low pH value; ammonia-nitrogen values of all the experimental groups are lower than 1100 mg/L; there is no fermentation inhibition, and the COD value recovers to the level of the blank sludge group after variation; the anaerobic fermentation system is in a steady status under self-regulation.

II. Comparison of Biogas Production from Waste Liquid

Figure 5:
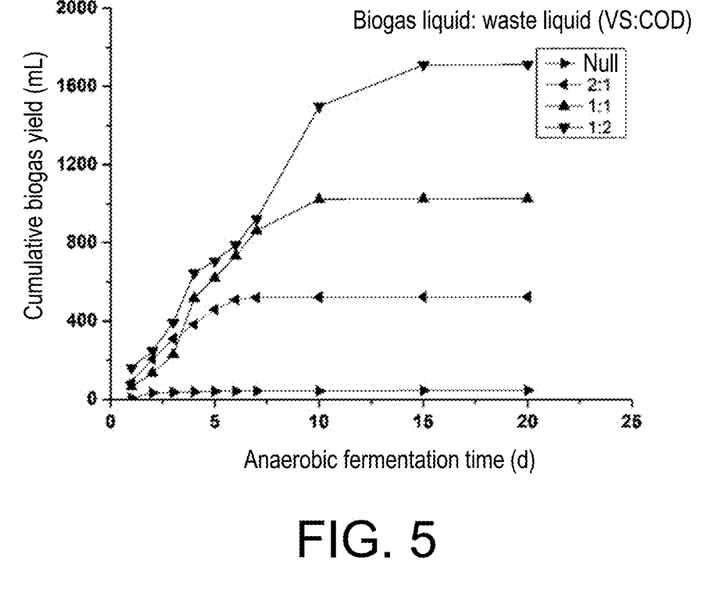
FIG. 5 shows a cumulative biogas yield from diosgenin waste liquid fermentation at different VS:COD ratios.

1. Variation of Accumulative Biogas Yield from Waste Liquid at Different VS Ratios As can be seen from FIG. 5, the accumulative biogas yield increases with the fermentation time, but the peak value of the biogas yield in each experimental group delays with the increase of the organic loading ratio. The fermentation group having an organic loading ratio of 2:1 achieves a peak value of the biogas yield basically after the fermentation is performed to the 7th day. When the fermentation is performed to the 10th day, the fermentation experimental group having an organic loading ratio of 1:1 has completed the effective fermentation; while when the high-load experimental group having a ratio of 1:2 performs continuous fermentation for 15 delays, the accumulative biogas yield and biogas production rate have no longer changed, and the cumulative curve is up to a stable and balanced linear state. At the end of the anaerobic fermentation of the diosgenin waste liquid, organic loadings of all the experimental groups were averaged to obtain the cumulative biogas production rate of each experimental group. The results are as follows: 326.9 mL/g COD (VS:COD=1:1)>318.7 mL/g COD (VS:COD=2:1)>277.7 mL/g COD (VS:COD=1:2). Thus as can be seen, when the organic loading ratio is VS:COD=1:2, the biogas production rate of the diosgenin waste liquid is the lowest; the reason why the efficiency is low may be as follows: the addition of lots of carbohydrates, acids and other substances in the system destroys the acid-base balance in the anaerobic fermentation system such that the enzymatic activity reduces and meanwhile the threshold value of the maximum transformation and utilization capacity of microbial flora in the anaerobic fermentation system is exceeded. The biogas production rate of the fermentation at a low load of VS:COD=2:1 is less than the biogas production rate at a ratio of 1:1. The above result not only indicates that the anaerobic fermentation system consisting of activated sludge has superior buffer capacity, but also indicates that the diosgenin waste liquid may be directly utilized to the maximum extent to satisfy the biogas production potential of the fermented microbial flora, such that the capacity of the anaerobic flora to utilize substrate reaches the saturation point. Therefore, the waste liquid produced after diosgenin extraction by aluminum chloride may produce biogas via anaerobic fermentation. Moreover, the maximum biogas production rate may be up to 326.9 mL/g COD at the organic loading of VS:COD=1:1.

Figure 6:
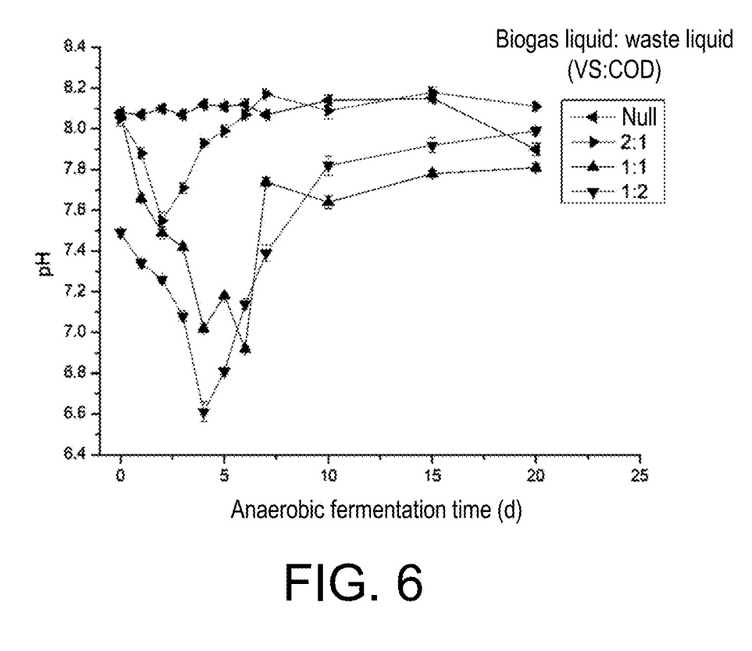
FIG. 6 shows pH variation during diosgenin waste liquid fermentation at different VS:COD ratios.
Figure 8:
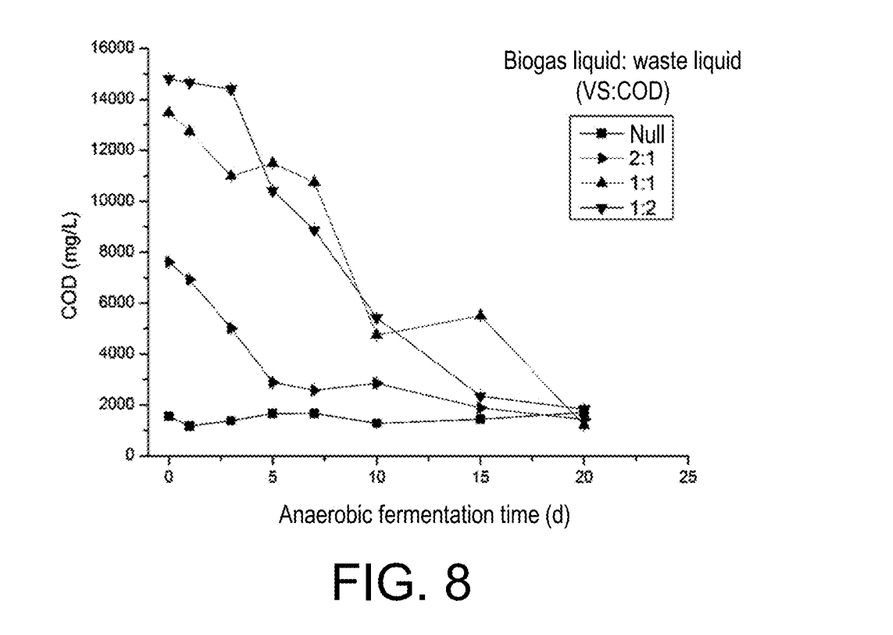
FIG. 8 shows COD variation during diosgenin waste liquid fermentation at different VS:COD ratios.

2. Study on the Physical and Chemical Properties of Waste Liquid with Different VS Ratios Under Anaerobic Fermentation (1) pH Variation FIG. 6 is a pH variation curve in a fermentation flask of the diosgenin waste liquid; at the beginning of the fermentation, affected by the weak acidity of the diosgenin waste liquid itself, the experimental group with the highest COD content has a pH value obviously lower than that of other experimental groups in the initial stage. Generally, for all the experimental groups with different loads, the pH value shows a trend of decreasing first and then increasing, which is basically consistent with the acid-base variation of the anaerobic fermentation in four stages. The fermentation of diosgenin waste liquid differs from the fermentation of *Dioscorea* waste residue in that the diosgenin waste liquid is an acidic solution with high COD content, with the increase of the organic loading, the COD content in the fermentation broth also increases. Meanwhile, the volume of the acid waste liquid added to the fermentation broth increases accordingly; therefore, the amplitude of pH variation is intensive as well. Moreover, too high organic loading may cause irreversible damage on the buffer capacity of the fermentation broth; too low pH value is easy to cause acidosis. The buffer capacity of the buffer system formed by volatile fatty acids and ammonia nitrogen in the anaerobic fermentation system may neutralize the weak acidity of the diosgenin waste liquid. When the diosgenin waste liquid has a VS:COD of 1:2, the pH value reduces to the minimum, being about 6.5, on the 4th day of the fermentation; afterwards, on the 5th day to the 10th day of the fermentation, as anaerobic microbial flora start to utilize small molecule acids and other substances to produce methane, the pH value gradually recovers to rise and slowly tends to be the pH value of the blank group. The pH variation curve is identical to and corroborated to that in FIGS. 5 and 8. Other experimental groups are similar thereto. To sum up, the pH variation of the *Dioscorea composita* waste liquid during anaerobic fermentation is kept within the normal range; there is no irreversible acidification caused by too low pH value, and the system is always in a steady operation status.

(2) $NH_3$—N Variation

Figure 7:
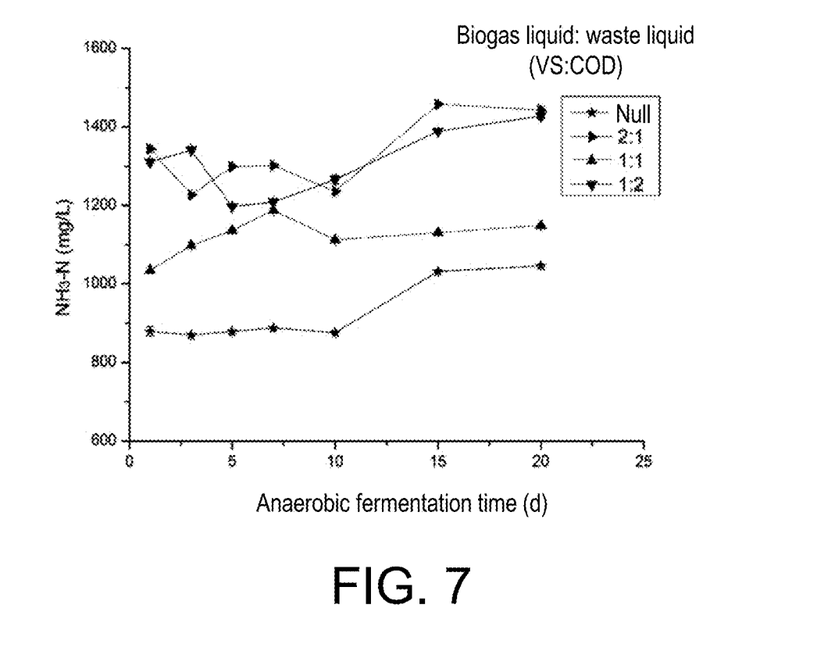
FIG. 7 shows $NH_3$—N variation during diosgenin waste liquid fermentation at different VS:COD ratios.

As can be seen from FIG. 7, $NH_3$—N has a very small amplitude of variation during the fermentation of the diosgenin waste liquid at different VS:COD ratios. Moreover, the $NH_3$—N value in each experimental group is higher than that of the blank group and the $NH_3$—N concentration is higher than 1000 mg/L; this is probably because nitrogenous organic compounds contained in the diosgenin waste liquid produce free ammonia under the degradation of microbial flora. Throughout the fermentation, ammonia-nitrogen values of all the experimental groups are lower than 1500 mg/L; the anaerobic fermentation system is in a steady status under self-regulation, and there is no fermentation inhibition. The fluctuation variation trend of the $NH_3$—N concentration at different VS:COD ratios is basically similar to that of the seeding sludge.

(3) COD Variation

High content of COD in the stock diosgenin waste liquid represents high content of available carbohydrates, fatty acids and other organic matters. After activated sludge and sugary waste liquid were mixed at different VS:COD ratios, the initial COD concentration was tested, and then the trend of the variation curve of the COD value was observed during the fermentation. As can be seen from FIG. 8, in a fermentation cycle, at the beginning of the fermentation, the initial COD concentration of the experimental group is different due to different VS:COD ratios; the higher the organic loading is, the higher the COD concentration of the experimental group is. Afterwards, under the fermentation by anaerobic bacteria, the COD concentration reduces gradually till recovers to the level of the blank sludge group. From the aspect of overall process, it shows an overall trend of slope decline. When the activated sludge and the sugary waste liquid have different VS:COD ratios of 2:1, 1:1 and 1:2, respectively, the COD removal rates of the fermentation broth are 81.41%, 91.11% and 87.46%, respectively; the fermentation group with VS:COD=1:1 has the highest COD removal rate, which is consistent with the result that there is a highest biogas production rate at such a ratio. Apparently, too high organic loading will cause an adverse impact on the COD removal rate; when the organic loading is lower, the COD removal rate is low, which is probably because the utilization of substrate by anaerobic flora is unsaturated, leading to not enough vigorous metabolic activity to affect the activity of the enzyme.

As can be seen from the above results: 326.9 mL/g COD (VS:COD=1:1)>318.7 mL/g COD (VS:COD=2:1)>277.7 mL/g COD (VS:COD=1:2). Therefore, the waste liquid produced after diosgenin extraction by aluminum chloride may produce biogas via anaerobic fermentation. Moreover, the maximum biogas production rate may be up to 326.9 mL/g COD at the organic loading of VS:COD=1:1. $NH_3$—N has a small amplitude of variation during the fermentation of diosgenin waste liquid; the ammonia-nitrogen value is lower than 1500 mg/L and the pH variation is within the normal range. The COD removal rates of the fermentation broth with different organic loadings are 81.41%, 91.11% and 87.46%, respectively; the fermentation group with VS:COD=1:1 has the highest COD removal rate, which is consistent with the result that there is a highest biogas production rate at such a ratio.

Example 2

(1) Preparation of diosgenin by hydrolysis of a ternary biphase $AlCl_3$: 5.0 g of the dried *Dioscorea* powder was added to a closed reactor; 80 mL 1.25 g/L aluminum chloride aqueous solution, 30 mL ethanol and 160 mL petroleum ether were added and mixed well, and subjected to reaction for 3.0 h at 130° C.; the reaction liquid was filtered to remove residues, and a petroleum ether layer was isolated, then rotary evaporation was carried out, and then recrystallization was performed to obtain diosgenin. Solid residue after the diosgenin extraction from *Dioscorea composita* by aluminum chloride was washed with water and dried, then stored in a drying vessel for further use.

(2) Biogas production from waste residue: the same as that in Example 1.

(3) Biogas production from waste liquid: the same as that in Example 1.

Example 3

(1) Preparation of diosgenin by hydrolysis of a ternary biphase $AlCl_3$: 5.0 g of the dried *Dioscorea* powder was added to a closed reactor; 80 mL 15 g/L aluminum chloride aqueous solution, 75 mL ethanol and 40 mL petroleum ether were added and mixed well, and subjected to reaction for 0.5 h at 180° C.; the reaction liquid was filtered to remove residue, and a petroleum ether layer was isolated, then rotary evaporation was carried out, and then recrystallization was performed to obtain diosgenin. Solid residue after the diosgenin extraction from *Dioscorea composita* by aluminum chloride was washed with water and dried, then stored in a drying vessel for further use.

(2) Biogas production from waste residue: the same as that in Example 1.

(3) Biogas production from waste liquid: the same as that in Example 1.

Example 4

(1) Preparation of diosgenin by hydrolysis of a ternary biphase $AlCl_3$: 5.0 g of the dried *Dioscorea* powder was added to a closed reactor; 80 mL 10 g/L aluminum chloride aqueous solution, 50 mL ethanol and 100 mL petroleum ether were added and mixed well, and subjected to reaction for 1.5 h at 155° C.; the reaction liquid was filtered to remove residue, and a petroleum ether layer was isolated, then rotary evaporation was carried out, and then recrystallization was performed to obtain diosgenin. Solid residue after the diosgenin extraction from *Dioscorea composita* by aluminum chloride was washed with water and dried, then stored in a drying vessel for further use.

(2) Biogas production from waste residue: the same as that in Example 1.

(3) Biogas production from waste liquid: the same as that in Example 1.

What is claimed is:

1. A method for producing biogas from a waste liquid/residue after diosgenin extraction by aluminum chloride, comprising:
   adding an anaerobic sludge and a waste residue from diosgenin extraction by aluminum chloride with an organic loading having a volatile solids ratio of (1-3):(1-2) or adding a seeding sludge and a diosgenin waste liquid with an organic loading having a VS:COD ratio of (1-2):(1-2) in a fermentation vessel, wherein the VS is the volatile solid of the seeding sludge, and the COD is a chemical oxygen demand of the diosgenin waste liquid; and
   subjecting the above components to fermentation at 35° C.-37° C. for 5-25 days to produce biogas,
   wherein the fermentation is performed with stirring for 1-2 min at intervals of 5-6 min.

2. The method according to claim 1, wherein the fermentation lasts for 5-15 days.

3. The method according to claim 1, wherein the seeding sludge has a pH value of 7.3-7.8 and a COD of 1000-1200 mg/L.

4. The method according to claim 1, wherein the volatile solids ratio of the anaerobic sludge to the waste residue from diosgenin extraction by aluminum chloride is 3:1; the VS:COD ratio of the seeding sludge to the diosgenin waste liquid is 1:1.

5. The method according to claim 1, wherein the diosgenin extraction by aluminum chloride is performed as follows: putting a dried *Dioscorea* powder to a reaction still, and adding a ternary biphase solution consisting of an aluminum chloride aqueous solution, ethanol and petroleum ether, and mixing well, performing a reaction for 0.5-3.0 h at 130-180° C., and filtering a reaction liquid to remove residues, isolating a petroleum ether layer, then performing rotary evaporation, and performing recrystallization to obtain diosgenin.

6. The method according to claim 5, wherein the reaction is performed at 140-170° C. for 1-2.5 h.

7. The method according to claim 5, wherein the aluminum chloride aqueous solution has a concentration of 1.25 g/L-15 g/L.

8. The method according to claim 5, wherein the ethanol/aluminum chloride aqueous solution/petroleum ether solution has a volume ratio of (6-15):16:(8-32).

9. The method according to claim 5, wherein an additive amount of the *Dioscorea* powder to the reaction system is 18-20 g/L.

* * * * *